(12) United States Patent
Pettett

(10) Patent No.: US 7,213,916 B1
(45) Date of Patent: May 8, 2007

(54) UNIVERSAL TEMPLE BAR HEARING PROTECTION DEVICE

(76) Inventor: Dawayne T. Pettett, 521 Twin View Dr., Sequim, WA (US) 98382

( * ) Notice: Subject to any disclaimer, the term of this patent is extended or adjusted under 35 U.S.C. 154(b) by 0 days.

(21) Appl. No.: 11/325,940

(22) Filed: Jan. 5, 2006

(51) Int. Cl.
*G02C 1/00* (2006.01)

(52) U.S. Cl. ...................................... 351/158; 351/123

(58) Field of Classification Search ............... 351/111, 351/117, 122, 123, 158
See application file for complete search history.

(56) References Cited

U.S. PATENT DOCUMENTS

| | | | |
|---|---|---|---|
| 3,856,007 A | 12/1974 | Leight | |
| D262,491 S | 12/1981 | Ebert | |
| 5,074,375 A | 12/1991 | Grozil | |
| 5,475,449 A | 12/1995 | Pyle | |
| 5,541,677 A | 7/1996 | Huhtala | |
| 5,655,263 A * | 8/1997 | Stoller | 24/3.3 |
| 5,664,291 A | 9/1997 | Stoller | |
| 5,703,670 A | 12/1997 | Callard | |
| 6,067,664 A | 5/2000 | Cortes | |
| 6,074,060 A | 6/2000 | Bruce | |
| 6,082,855 A | 7/2000 | Fleming | |
| D435,058 S | 12/2000 | Green et al. | |
| 6,176,576 B1 | 1/2001 | Green et al. | |
| 6,233,345 B1 | 5/2001 | Urwyler | |
| 6,302,111 B1 | 10/2001 | Bremenstul | |
| 6,340,227 B1 | 1/2002 | Solberg et al. | |
| 6,604,823 B2 | 8/2003 | Hursey, Jr. | |
| 6,728,974 B2 | 5/2004 | Wadsworth | |
| 2003/0193645 A1 | 10/2003 | Gilmore et al. | |

* cited by examiner

Primary Examiner—Huy Mai
(74) Attorney, Agent, or Firm—Virginia P. Shogren, Esq.

(57) ABSTRACT

A hearing protection device readily insertable and removable from temple arms of eye glasses of varying size, width, angles and flanges, comprising a stiff but bendable vinyl tube, a connector cord, and an earplug. The tube is positioned around the temple bar of glasses past where the temple bar comes into contact with the user's ear when the glasses are worn. The device is held in position by pressure points of contact between the internal surface of the tube and points along the arm of glasses. Once mounted, and glasses worn, the sensation of the vinyl tube simulates the eyeglass arms themselves, and the earplug is conveniently positioned behind and outside of the user's line of vision. The earplug may be inserted and removed from the user's ears as desired given changing noise levels in the user's environment.

20 Claims, 4 Drawing Sheets

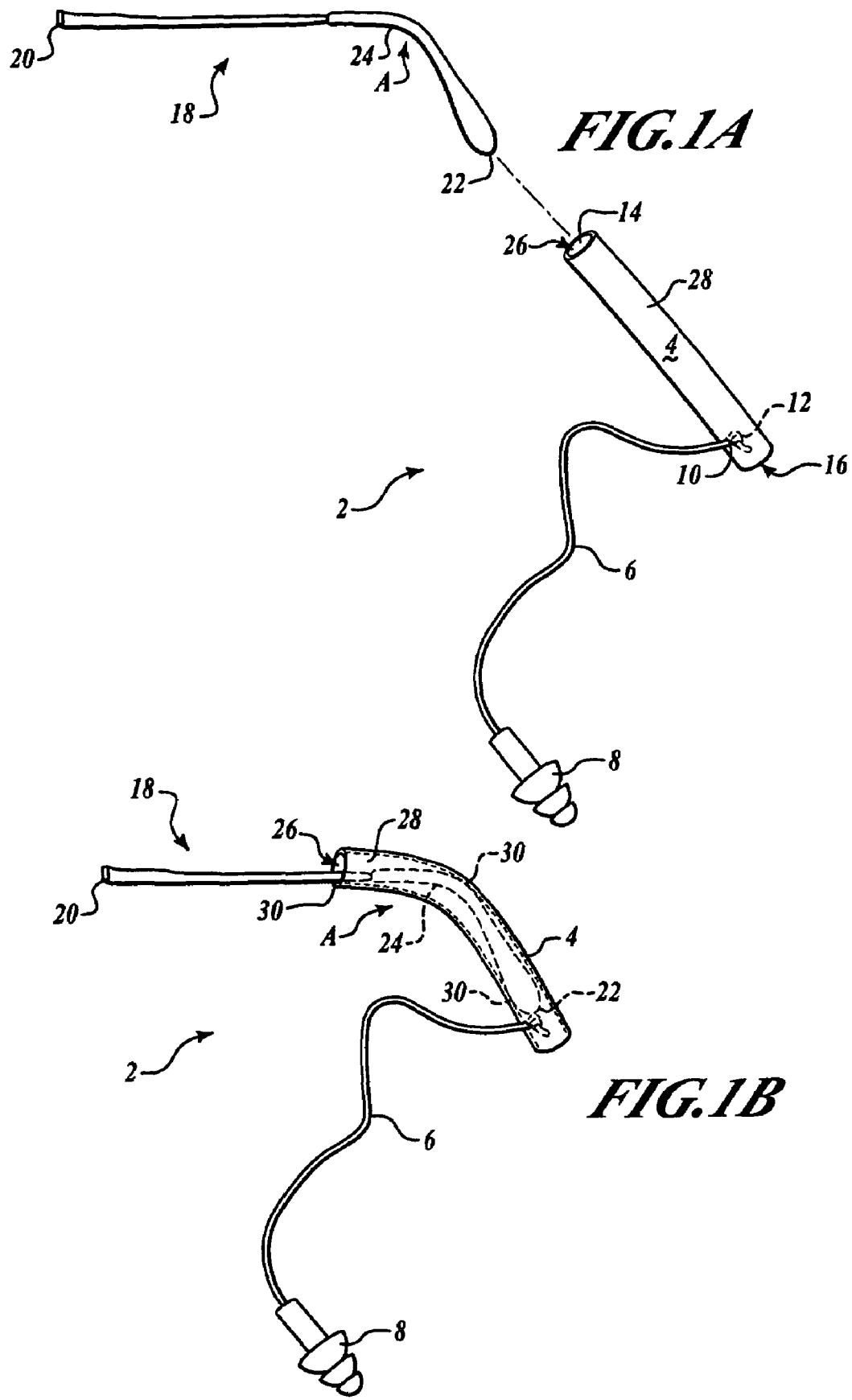

UNIVERSAL TEMPLE BAR HEARING PROTECTION DEVICE

FIELD

The invention relates generally to hearing protection devices with ear plugs to prevent damage to hearing, and more particularly, to devices used in combination with glasses to provide convenient use and availability of the ear plug to an individual.

BACKGROUND

There is a growing awareness for the importance of hearing protection through use of earplugs in high-noise environments. The need for ear protection arises in a variety of situations ranging from work-related noise (factories, chainsaws, lawn mowers), to entertainment and recreational venues, such as concerts, fireworks displays, large sports events, hunting, or target practice. Often in these situations, the earplug user is also wearing glasses—whether prescription glasses, sport glasses, sunglasses, or safety glasses. Given fashion trends, eyeglass designs now come in a wide range and variety—with some temple bars still in the traditional angled or bent shape for retention such as when the user bends over; while many other designs, including many types of safety glasses, are designed to have straight temple bars that also apply pressure to the sides of the user's head for retention. Some temple bars still reflect the traditional narrow size and design with minor flange at the distal end; other commonly seen designs have wider arms and/or large, flared/flanged ends for fashion purposes and/or to apply additional pressure against the user's head. Recent designs in safety glasses give them the appearance of sport glasses.

There are several earplug systems and devices in the prior art that may be used in combination with glasses. For example, U.S. Pat. No. 6,340,227 discloses an ear plug system either removably connected to the distal end of the arms of glasses or permanently positioned within the arms, wherein an ear plug is attached to a cord that is stored within a recoil device. The user draws the cord stored within the recoil device and thereafter inserts the earplug into the ear. The system is attached to the arm glasses by a connector designed to snugly fit about the distal end of the arms of glasses.

U.S. Pat. No. 6,082,855 discloses an attachment for safety eyeglasses including a mount on the eyeglass temple bar, an earplug, and a coupling wire wound into a tight helix for storage between the rear of the outer ear and the skull to minimize earplug motion when the earplug is not inserted into the ear canal. The mount is a tube of elastomeric material (thermoplastic rubber) designed with a larger front end hole and a smaller rear end hole for expansion over the temple bar by elastic stretching resulting in high friction holding the mount to the temple bar. The elastic tube tightly grips the temple bar to avoid rattling.

U.S. Pat. No. 5,541,677 discloses a vision-hearing protection device including a retraction feature wherein earplugs may be quickly pulled in toward a retainer for storage. The ends of the device are designed to resiliently stretch over and frictionally engage the arms of the glasses.

Common to each of these devices is the need for a user to apply fine motor control to insert the device through stretching of elastomeric or rubberized materials onto and over the distal ends of the arms of glasses. Secure mounting of the devices is not possible unless the distal ends of the glasses are shaped such that the mounting portions of the device can fit tightly around them. The connector and mount systems in the prior art are designed for snug attachment and high friction connection over the distal ends of the eyeglass arms, thereby necessitating fine motor manual manipulation, time, and effort, to stretch and adequately position the systems onto the glasses. The systems cannot be mounted and removed on different shaped ends of eyeglass arms, including large, flange-ended eyeglass arms. They present a particular challenge for mounting onto glasses when wearing gloves. Given the need for the devices to snugly fit around and against the distal ends of arms of glasses for high-friction contact, the systems are severely limited in the type, shape and width of arms upon which they can be mounted and are not easy to mount.

Accordingly, there is an unmet need in the prior art for an earplug device to be used in combination with eyeglasses that is quick and simple to insert and remove from the temple bars of eyeglasses of various designs, angles, shapes and widths, yet which is secure, comfortable, and hardly noticeable to the wearer of the device.

THE INVENTION

Summary, Including Objects and Advantages

The inventive universal temple bar hearing protection device comprises a stiff, but bendable elongate tube having a first forward end open to permit insertion of an eyeglass temple bar inside the tube past the point where the ear would otherwise come into contact with the arms of the glasses when the glasses are worn on the wearer's head. A connector cord is attached to the tube, and an earplug is attached to the connector cord.

The tube, once encircling the temple bar (also referred to herein as eyeglass arm) past the ear contact point, is held in position through a limited number of pressure points of contact between the internal surface of the tube and the arm of glasses. The tube takes the place of the temple bars; simulates the feeling of the temple bars to the wearer, and as such, is not noticeable and comfortable to the wearer.

Once the device has been inserted over and around one or both eyeglass arms, the user may wear the glasses and place the earplug(s) hanging from the cord(s) into the user's ear(s) as desired. When not needed, the earplug hangs freely from the tube but remains available for reinsertion as desired. The earplugs are behind the user's ears, remain outside the user's line of vision, and do not present a hazard.

When finished using the device, the user may remove the glasses and pull the tube off the temple bar, which is accomplished easily and quickly given the limited number of pressure points holding the device in position. When not being worn, the device fits easily in a user's pocket.

The preferred embodiment comprises a vinyl tube approximately 2–3 inches (5–8 cm) in length with an inside diameter of ¼ inches (6.35 mm) and a thickness of ¹⁄₁₆ inches (1.58 mm). The length of the stiff, elongate tube allows the device to be held and handled easily by the user during insertion and removal; the preferred diameter allows the device to be inserted over and around arms of glasses of various widths and shapes (e.g., angled, straight, flanged, no-flange), and the thin wall of the tube assists in simulating the feel of the temple bar when the glasses are worn.

BRIEF DESCRIPTION OF THE DRAWINGS

The invention is described in more detail with reference to the drawings, in which:

FIG. 1a is a side elevation view of the device next to an eyeglass arm;

FIG. 1b is a side elevation view of the device inserted over and encircling the eyeglass arm;

DETAILED DESCRIPTION, INCLUDING THE BEST MODES OF CARRYING OUT THE INVENTION

Figure 2A:
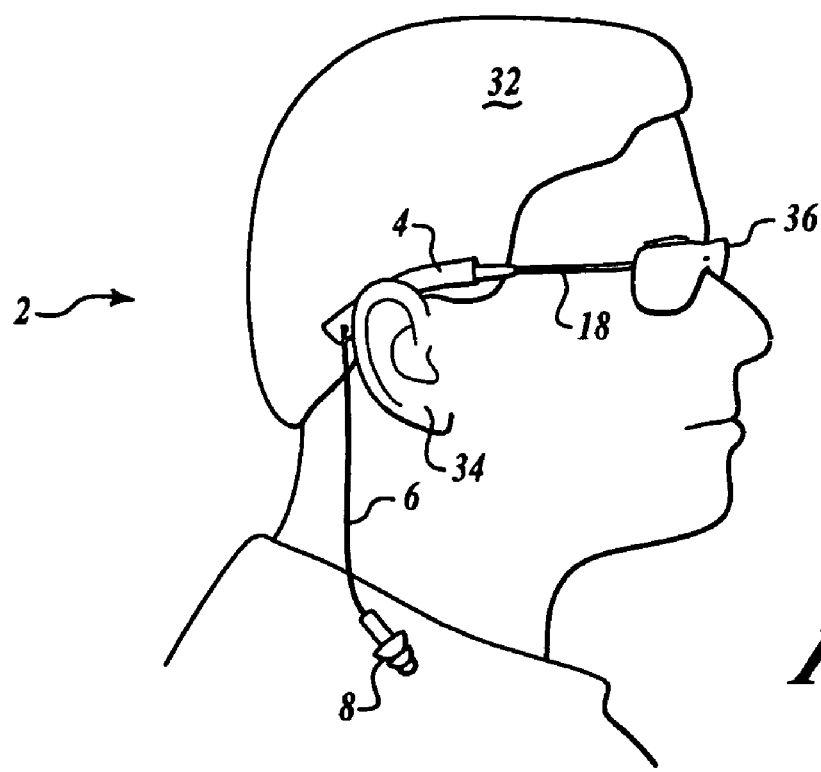
FIG. 2a is a side elevation view of the device inserted on an eyeglass arm with glasses worn by a user with earplug extended.

The following detailed description illustrates the invention by way of example, not by way of limitation of the scope, equivalents or principles of the invention. This description will clearly enable one skilled in the art to make and use the invention, and describes several embodiments, adaptations, variations, alternatives and uses of the invention, including what is presently believed to be the best modes of carrying out the invention.

In this regard, the invention is illustrated in the several figures, and is of sufficient complexity that the many parts, interrelationships, and sub-combinations thereof simply cannot be fully illustrated in a single patent-type drawing. For clarity and conciseness, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

All publications, patents and applications cited in this specification are herein incorporated by reference as if each individual publication, patent or application had been expressly stated to be incorporated by reference.

Referring to FIGS. 1a and 1b, an example of the preferred embodiment of the present invention is illustrated and generally indicated by the reference numeral 2. FIG. 1a shows the device 2 adjacent to, but not yet inserted onto, an eyeglass arm 18 (also referred to herein as a temple bar). The device 2 comprises a stiff but bendable elongate tube 4 having a first end opening 14, a second end opening 16, an internal surface 26 and an external surface 28. Connector cord 6 is attached to tube 4 by internal knot 12 in the connector cord 6. The cord 6 exits tube 4 though hole 10 and is attached to earplug 8. As shown in FIG. 1a, hole 10 is near the second end 16 of tube 4 but may be positioned at any suitable location along tube 4.

FIG. 1b shows the device 2 inserted over and encircling the eyeglass arm/temple bar 18. The eyeglass arm 18 has a distal end 22, a temple end 20, and an intermediate ear contact point 24 where the top of a user's ear (not shown) comes into contact with the eye glass arm 18 when the glasses are being worn. The ear contact point 24 falls at a point between, but not necessarily midway between, the distal 22 and temple 20 ends of the eyeglass arm 18.

As shown in FIG. 1b, the eye glass arm 18 has been inserted inside tube 4 past ear contact point 24. Tube 4 encircles arm 18 from its distal end 22 to and past the ear contact point 24. Once inserted, the internal surface 26 of tube 4 comes into contact with eye glass arm 18 at a limited number, but at least two, compression/pressure points 30. The tube 4 is slightly bent as a result of being pushed past angle "A" in the eyeglass arm 18. As shown in FIG. 1b, the device is held in position by contact pressure points 30.

In the preferred embodiment, tube 4 is made of vinyl tubing (clear or opaque/colored) with an inside diameter of ¼ inches (6.35 mm), an outside diameter of ⅜ inches (9.52 mm), a wall width of $1/16^{th}$ inches (1.58 mm), a hardness Shore of 68 and a tensile strength of PSI 2000. Tube 4 can be of any suitable length, diameter and width to permit the device 2 to be easily inserted and removed past the ear contact point 24 on the eyeglass arm 18. The inside diameter of tube 4 optimally equals or exceeds the widest portion of the eye glass arm 18 between its distal end 22 and the ear contact point 24. The tube 4 may be circular or oval, or a combination of both.

Tube 4 may be constructed of any material sufficiently stiff but bendable so as to create a limited number of contact pressure points along the eyeglass arm to facilitate simple and quick insertion and removal of the device 2. Tube 4 may have its second end 16 open or closed. The external surface 28 of the tube 4 may be striated, grooved, ribbed, channeled, or otherwise modified to provide improved grip to the user when inserting and removing the device 2.

In the preferred embodiment, cord 6 is a plastic wire approximately 6 inches (15.24 cm) in length. Cord 6 may be constructed of any material(s) sufficiently flexible to allow the ear plug 8 to be moved to the desired position within the ear canal of a user. One skilled in the art will also appreciate that cord 6 could be of any length or suitable design to conveniently keep the ear plug 8 in position generally proximate the user's ear. Cord 6 may be connected to the tube and/or ear plug 8 permanently by any suitable means, or removably attached if desired for safety or other reasons.

The ear plug 8 may be of any suitable design or shape to prevent noise-related damage to the inner ear. The ear plug 8 could include a tab or handle or other structure for easy manipulation of the ear plug 8 when inserting or removing the ear plug 8 from the user's ear 34. The ear plug 8 may be removably attached to connector cord 6 for replacement with a new or differently designed ear plug 8, or for washing and replacement of the same ear plug 8 for sanitary purposes.

FIG. 2a shows a user 32 wearing the device 2 on eye glasses 36 prior to inserting the earplug 8 into his ear 34. Referring to FIG. 2a, earplug 8 is shown hanging by attachment to cord 6. Tube 4 is comfortably positioned above the user's ear 34 where the eye glass arm 18 would otherwise be in contact with the top of the user's ear 34. Eyeglasses 36 may be of any type, with temple bars of any shape, design, angle, width or flange width, including without limitation, prescription glasses, sunglasses, sport glasses and safety glasses.

As shown in FIG. 2a, the user 32 has inserted the device 2 over temple bar 18, and has positioned the glasses 36 on the head as he would normally wear glasses. Tube 4 encircles the eyeglass arm 18 such that the device 2 is comfortable and hardly noticeable to the user 32. The user 32 may optionally, and ideally, insert the device on both temple bars 18 of the eyeglasses 36 (as shown in FIG. 3) so that the glasses 36, when worn, are level.

Figure 2B:
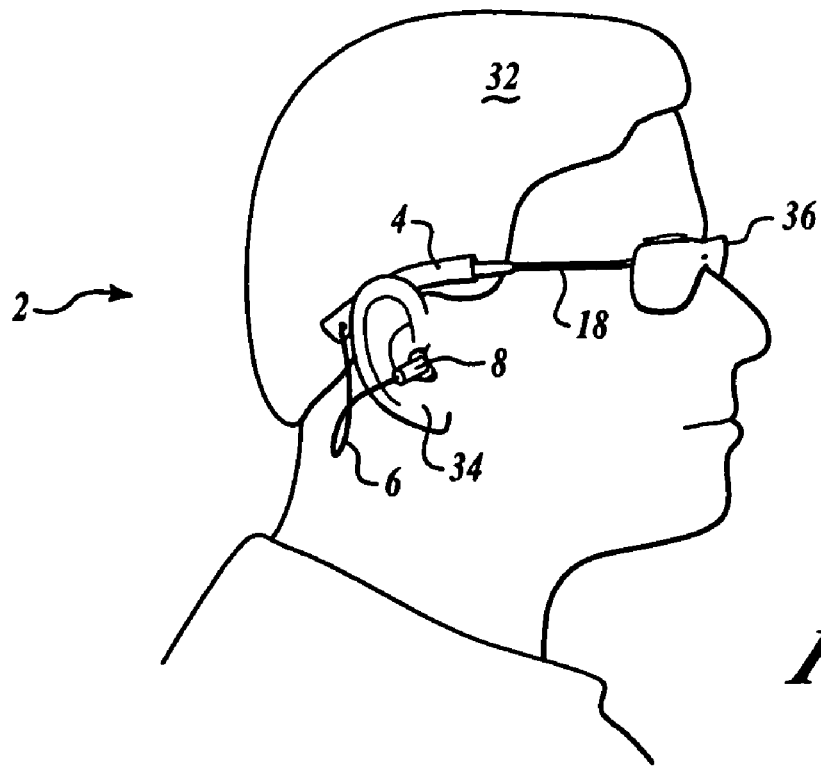
FIG. 2b is a side elevation view of the device inserted on an eyeglass arm with glasses worn by a user with earplug inserted into the user's ear.

FIG. 2b shows a user 32 wearing the device 2 on eye glasses 36 after inserting the earplug 8 into his ear 34.

Figure 3:
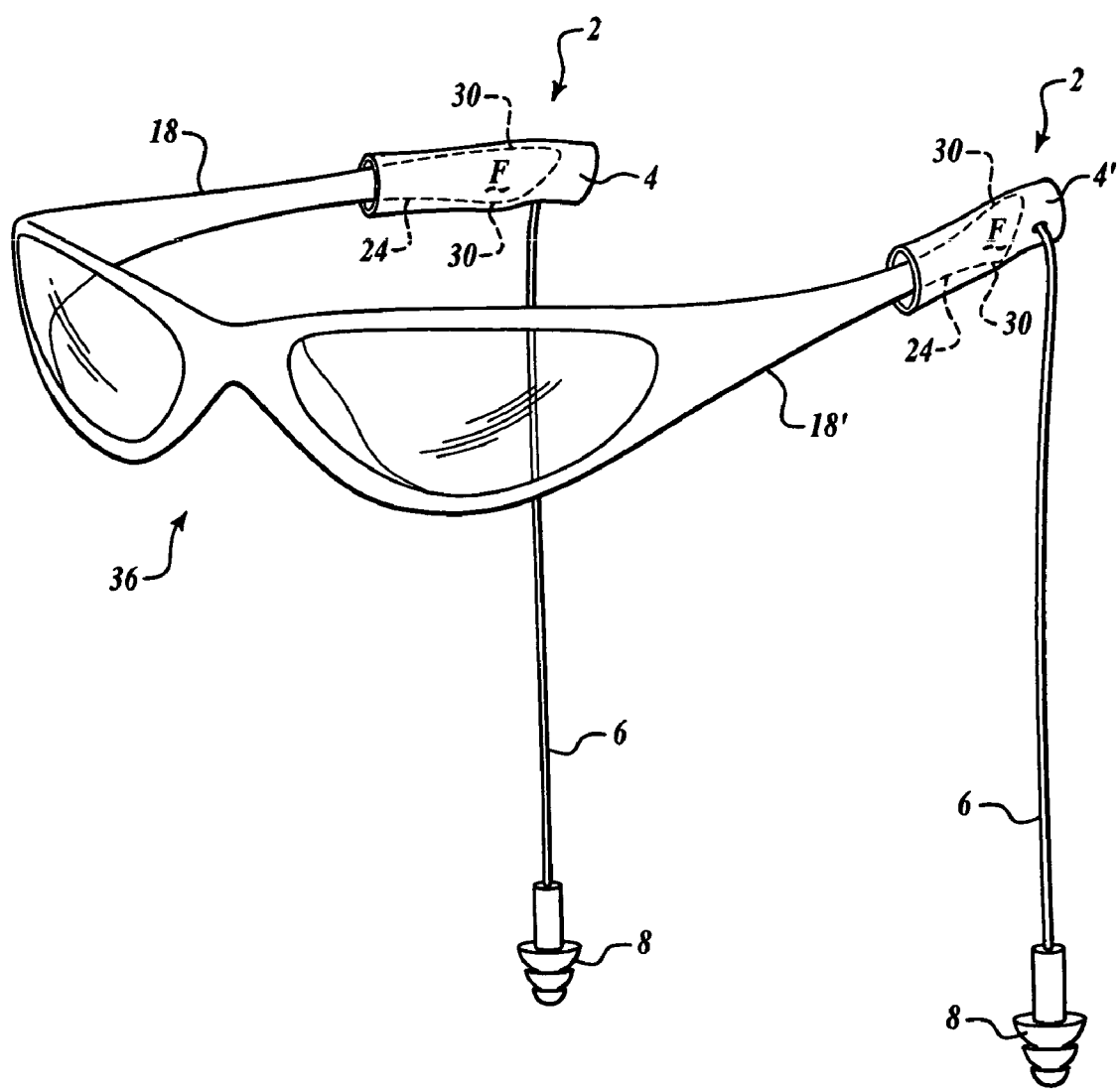
FIG. 3 is a top perspective view of the device inserted on both arms of eyeglasses.

FIG. 3 shows the device 2 inserted around both arms 18/18' of eyeglasses 36. The eyeglass arms 18, 18' shown in FIG. 3 are not angled (as shown in FIGS. 1a and 1b) and have a wider flange marked with an "F". The device 2 is positioned along arms 18/18' shown in FIG. 3 through insertion of the arms 18/18' inside tubes 4/4' past the ear contact points 24/24'. Tubes 4/4' encircle arms 18/18'. Pressure points 30, where tubes 4/4' come into contact with points along the eye glass arms 18/18', hold the device 2 in position.

Figure 4:
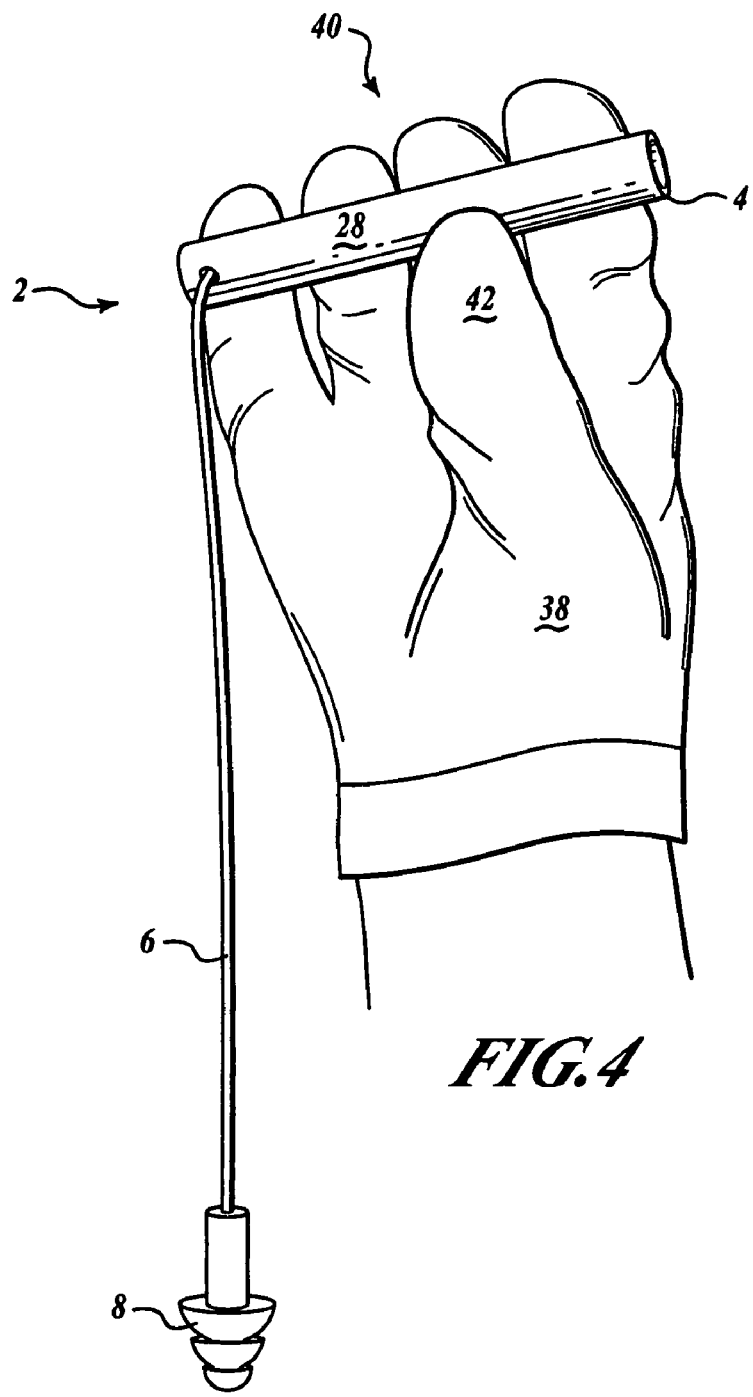
FIG. 4 is a perspective view of a gloved hand holding the device.

FIG. 4 shows a gloved hand 38 of a user holding device 2. As shown in FIG. 4, the device 2 may be handled and manipulated by a covered hand for insertion and removal. The device 2 allows for application of fingers 40 on one side of the device 2 with thumb 42 support from below.

Figure 5:
FIG. 5 is a side elevation view of the tube portion of the device with indicia.

Referring to FIG. 5, the external and/or internal surfaces of the tube 4, may optionally include printed, embossed, or otherwise applied indicia 44, including without limitation, indicia to identify the user's name (for, example, for sanitary purposes of not confusing ear plugs between different users), and/or to identify the manufacturer's name or company logo. The tube 4 may be clear or opaque, may be personalized or designed as a fashion-statement through use of different patterns, designs, and/or colors.

INDUSTRIAL APPLICABILITY

It is clear that the inventive hearing protection device of this application has wide applicability to the hearing protection industry, namely to providing earplug protection in combination with eyeglasses that is quick and simple to insert and remove from the temple bars of eyeglasses of various designs, shapes and widths, yet which is secure, comfortable, and hardly noticeable to the wearer of the device.

The device may be used in a variety of situations, and on a variety of different-shaped eye glass temple bars, from the traditional bent temple bar, to the more modern straight, but flared temple bars. The device is simple in design, inexpensive to manufacture, easy to store, carry and use, and does not require fine motor control or manual manipulation of elastomeric or rubberized surfaces for mounting. As such, a user can both mount and remove the device to the user's glasses quickly and easily and can even insert or remove the device when wearing gloves.

Thus, the inventive device has the clear potential of becoming adopted as the new standard device for earplug use when wearing glasses.

It should be understood that various modifications within the scope of this invention can be made by one of ordinary skill in the art without departing from the spirit thereof and without undue experimentation. For example, the tube can have a wide range of designs to provide the functionalities disclosed herein, including modifications to increase grip, a closed end, and/or personalized or company indicia printed or embossed thereon. This invention is therefore to be defined by the scope of the appended claims as broadly as the prior art will permit, and in view of the specification if need be, including a full range of current and future equivalents thereof.

I claim:

1. A hearing protection device for insertion over one or more arms of a pair of glasses, said one or more arms of said glasses each having a rear distal end, a front temple end, and an intermediate ear contact point, said device comprising:

an elongate tube having a first end and a spaced, opposed second end, and an internal surface and an external surface, said first end being open to permit insertion of the arm inside the tube;

a connector cord attached to said tube;

an earplug attached to said connector cord; and, wherein said tube encircles the rear distal end of the arm and past the ear contact point simulating a feeling of a temple bar of a wearer of the device.

2. The device of claim 1 wherein the tube is held in position encircling the arm by at least two pressure points of contact between the internal surface of the tube and the arm.

3. The device of claim 1 wherein the tube is stiff but bendable.

4. The device of claim 1 wherein said tube is constructed of vinyl tubing.

5. The device of claim 1 wherein a diameter of said tube equals or exceeds a widest point along the arm of glasses between the rear distal end and the ear contact point.

6. The device of claim 1 wherein at least a portion of said external surface of said tube is modified to improve grip of a user of the device.

7. The device of claim 1 wherein said tube includes informational indicia disposed on the external and/or internal surfaces.

8. The device of claim 1 wherein said second end of the tube is closed.

9. The device of claim 1 wherein the connector cord is attached to said tube by a knot tied in the connector cord running through a hole in the tube.

10. The device of claim 1 wherein the earplug is removably attached to said connector cord.

11. A hearing protection system, comprising:

glasses having a frame, a first arm, and a second arm, each of said arms having a rear distal end, a front temple end, and an intermediate ear contact point;

an earplug system inserted over one or both of said arms, each of said earplug systems comprising:

an elongate tube having a first end and a spaced, opposed second end, and an internal surface and an external surface, said first end being open to permit insertion of the arm inside the tube;

a connector cord attached to said tube;

an earplug attached to said connector cord; and, wherein said tube encircles the rear distal end of the arm and past the ear contact point simulating a feeling of a temple bar of a wearer of the system.

12. The hearing protection system of claim 11 wherein said tube is held in position encircling the arm by at least two pressure points of contact between the internal surface of the tube and the arm.

13. The hearing protection system of claim 11 wherein the tube is stiff but bendable.

14. The hearing protection system of claim 11 wherein said tube is constructed of vinyl tubing.

15. The hearing protection system of claim 11 wherein a diameter of said tube equals or exceeds a widest point along the arm of glasses between the rear distal end and the ear contact point.

16. The hearing protection system of claim 11 wherein at least a portion of said external surface of said tube is modified to improve grip of a user of the system.

17. The hearing protection system of claim 11 wherein said tube includes informational indicia disposed on the external and/or internal surfaces.

18. The hearing protection system of claim 11 wherein said second end of the tube is closed.

19. The hearing protection system of claim 11 wherein the connector cord is attached to said tube by a knot tied in the connector cord running through a hole in the tube.

20. The hearing protection system of claim 11 wherein the earplug is removably attached to said connector cord.

* * * * *